United States Patent
Lemke

Patent Number: 5,615,938
Date of Patent: Apr. 1, 1997

[54] DEVICE FOR ILLUMINATING OBJECTS IN PARTICULAR THOSE TO BE RECORDED WITH A VIDEO CAMERA

[76] Inventor: Norbert Lemke, Danziger Str. 21, D-82194 Gröbenzell, Germany

[21] Appl. No.: 137,173
[22] PCT Filed: Feb. 15, 1993
[86] PCT No.: PCT/DE93/00127
§ 371 Date: Oct. 14, 1993
§ 102(e) Date: Oct. 14, 1993
[87] PCT Pub. No.: WO93/16326
PCT Pub. Date: Aug. 19, 1993

[30] Foreign Application Priority Data

Feb. 14, 1992 [DE] Germany ............... 42 04 486.3

[51] Int. Cl.⁶ .................................. G03B 15/02
[52] U.S. Cl. ................... 362/18; 362/17; 362/32; 362/272; 362/277; 362/285; 362/293; 348/370
[58] Field of Search ...................... 348/370, 371; 362/3, 5, 8, 11, 12, 16–18, 32, 271, 272, 286, 287, 270, 280, 277, 293; 385/88, 89, 90, 93, 117

[56] References Cited

U.S. PATENT DOCUMENTS

| | | | |
|---|---|---|---|
| 1,446,248 | 2/1923 | Foster et al. | 362/270 |
| 1,910,989 | 5/1933 | Hanks | 362/3 |
| 2,621,569 | 12/1952 | Glassey | 362/3 |
| 3,446,951 | 5/1969 | Schmidt | 362/3 |
| 3,638,008 | 1/1972 | Keller et al. | 362/32 |
| 3,665,179 | 5/1972 | McLintic | 362/280 |
| 3,783,261 | 1/1974 | Hartmann | 362/18 |
| 3,914,013 | 10/1975 | Rosenberg | 385/117 |
| 3,926,501 | 12/1975 | Hama | 362/270 |
| 4,011,403 | 3/1977 | Epstein et al. | 348/370 |
| 4,300,167 | 11/1981 | Miller et al. | 348/370 |
| 4,361,863 | 11/1982 | Hagner | 362/280 |
| 4,423,940 | 1/1984 | Kashihara et al. | 362/18 |
| 4,425,599 | 1/1984 | Rieder et al. | 362/280 |
| 4,561,429 | 12/1985 | Sato et al. | 348/371 |
| 4,754,328 | 6/1988 | Barath et al. | 385/93 |
| 4,829,407 | 5/1989 | Bushell et al. | 362/293 |
| 4,881,128 | 11/1989 | Yamada | 348/370 |
| 4,997,254 | 3/1991 | Ganev | 385/90 |
| 5,016,975 | 5/1991 | Sasaki et al. | 385/117 |
| 5,021,928 | 6/1991 | Daniel | 362/293 |
| 5,040,320 | 8/1991 | Reidinger | 362/32 |
| 5,083,253 | 1/1992 | Hahnel | 362/280 |

Primary Examiner—Ira S. Lazarus
Assistant Examiner—Alan B. Cariaso
Attorney, Agent, or Firm—Antonelli, Terry, Stout & Kraus, LLP

[57] ABSTRACT

Disclosed is a device for illuminating objects, in particular those to be recorded by a video camera, having at least one lamp, the light of which a condenser system projects onto an optical system, which directs said light onto the object or objects to be illuminated, and a control means for controlling the intensity of the illumination with which the object is illuminated.

The present invention is distinguished by the control means moving, respectively pivoting, the lamp, the condenser system and/or the the optical system in the direction of the optical axis of the condenser system, respectively of the optical system and/or perpendicular thereto.

23 Claims, 4 Drawing Sheets

DEVICE FOR ILLUMINATING OBJECTS IN PARTICULAR THOSE TO BE RECORDED WITH A VIDEO CAMERA

TECHNICAL FIELD

The invention relates to a device for illuminating objects in particular those to be recorded with a video camera, the device having at least one lamp, the light of which projects via a condenser system onto an optical system which directs the light at the object or objects to be illuminated as well as having a control means for regulating the intensity of the light with which the object is to be illuminated.

There are numerous cases in which devices of this type are needed. Typical applications are in medical or technical video endoscopy or image processing, in particular, of technical scenes.

STATE OF THE ART

In the state of the art generic devices lamps, in particular, halogen lamps or arc lamps (Xenon, HMI, etc.), are employed. To control, respectively regulate, illumination brightness, a voltage regulation means is frequently utilized with halogen lamps, whereas in the case of arc lamps a mechanical motor shutter regulation means is usually employed.

Brightness control by means of lamp voltage, respectively the power of the lamp, has the disadvantage that the color temperature changes dependent on the voltage, respectively, the power. This is undesirable in both video endoscopy and image processing, because as a result there is a color shift in the picture. In particular, this type of control cannot be applied with arc lamps.

The use of a shutter, as by way of illustration, an iris stop, has the disadvantage that the shutter warms up too much. This warming up is not only unpleasant, but can also lead to distortion of the lamina. Furthermore, shading effects may occur.

DESCRIPTION OF THE INVENTION

The object of the present invention is to improve a device for illuminating objects, in particular, those to be recorded with by a video camera, the device having at least one lamp, the light of which projects via a condenser system onto an optical system, which directs the light at the object or objects to be illuminated and having a control means for regulating the intensity of the light with which the object is to be illuminated, in such a manner that illumination brightness can be quickly and reliably adjusted without using, in particular, mechanical shutters and without regulating the power of the lamp, i.e. in particular, without color shifting.

An element of the present invention is that the control means moves the lamp, the condenser system and/or the optical system in the direction of the optical axis of the condenser system, respectively of the optical system or in perpendicular direction thereto, respectively pivots one of the aforementioned elements.

In other words, an element of the present invention is that the position of the focus of the condenser system in relation to the optical system arranged thereafter is regulated while constant voltage, respectively constant power, is advantageously, but not necessarily applied to the lamp.

As it is not necessary to control and respectively regulate, lamp brightness, any lamps, by way of illustration the halogen lamps, but also arc lamps or other and, in particular, cost-favorable types of lamps, can be used in an invented device. In any event, the color temperature of the lamp does not change, because the point of operation of the lamp is not moved.

Furthermore, brightness control, respectively regulation, can occur utilizing little power, because the invented brightness control by shifting the focus position requires only small distances.

According to another embodiment, a control unit activates the control means. A manually entered or program-control-entered positioning signal, but also a control signal of a light measurement device, may be transmitted to the control unit. It is especially advantageous if the control signal is derived from a video signal from a video camera. Another embodiment sets forth that the control signal is derived from the output signal of the image recorder prior to signal processing by the camera electronics. This improvement has the advantage that the video camera amplification control means and the lamp control means do not generate mutual "pumping".

Moving the lamp in the direction of the optical axis, respectively in perpendicular direction thereto and/or pivoting the lamp, the condenser system and/or the optical system may, in principle, occur in any desired manner. Examples are the use of an electrodynamic system (claim 3) or a shape memory element whose temperature can be adjusted by means of a heating element (claim 4).

Moreover, as the sole adjustment means or as supplementary adjustment means, the control means can permit manual movement of the lamp, the condenser system and/or the optical system, by way of illustration, via an adjustment screw (claims 7, respectively 8).

Furthermore, for manual adjustment of lamp brightness, the control means may be provided with an adjustment device for the electric current flowing through the electrodynamic system, respectively the heating element (claim 9).

The invented device, has the advantage that reduction of brightness does not result in an increase in the infrared portion. This is especially advantageous if the optical system, like by way of illustration in video endoscopes, is provided with a fiberglass bundle that guides the light to the object to be illuminated, because the hot light can not "burn" the fibreglass bundle.

Nonetheless, it may be advantageous in a number of applications to provide an infrared-blocking filter (claim 10), which is arranged at an angle unequal to 90° with the optical axis of the condenser, respectively the optical system. By means of the diagonally positioned infrared-blocking filter, the IR radiation is reflected out of the beam path.

Placement of the lamp in an adapter has a number of advantages:

First it is possible to employ various adapters having different light-entry points and automatic focus adaption if the plug-in connections of the light-guides are of varying length.

Furthermore, the adapter may be designed as a screw-on rapid lamp changer at the rear wall. By this means the lamp support remains relatively cool and changing the lamp can occur from the rear side of the device, thus outside the sterile area in medical applications.

A further improvement of the present invention, which however may be utilized independent of; or in addition to, several of the above-described features is described as follows.

In condenser systems provided with a reflector for the light of the lamp, the following problem arises:

Due to the fusing point, which usually is centrally located, the light rays emerge from the reflector at an angle to the optical axis and thus likewise not in perpendicular direction into the light entry surface(s) of the fiberglass bundle so that there may be a considerable loss of light.

In accordance with the present invention, means are provided which guide the light rays emerging from the reflector almost in perpendicular direction into the light entry surface(s) of the fiberglass bundle.

These means may, by way of illustration, be a fanlike spreading of the fibreglass bundles which are designed in such a manner that the light emerging from the reflector on a surface of a cone enters into each of the single elements of the spread-out fibreglass bundle almost perpendicularly.

As an alternative or in addition, these means, may be provided with at least one lens which deflects the light emerging from the reflector on a surface of a cone in such a manner that it enters almost perpendicularly into the fiberglass bundle or bundles. This lens has perferably one surface which is not simply spherically curved but rather has differently curved areas, thus has several "calottes" which deflect the light on the surface of a cone into the optical axis of the system and, in particular of the fiberglass bundle.

It is especially preferable if the reflector, is mirrored in such a manner that infrared light can pass, because such an embodiment yields a "cold" light with no red shift and no heat-collecting infrared filter.

BRIEF DESCRIPTION OF THE DRAWING

The present invention is made more apparent by way of example in the following without the intention of limiting the scope or spirit of the overall inventive concept using preferred embodiments with reference to the drawing to which, moreover, is to be expressly referred with regard to the disclosure of all invented details not explained more explicitly in the text. Shown are.

DESCRIPTION OF PREFERRED EMBODIMENTS

Figure 1:
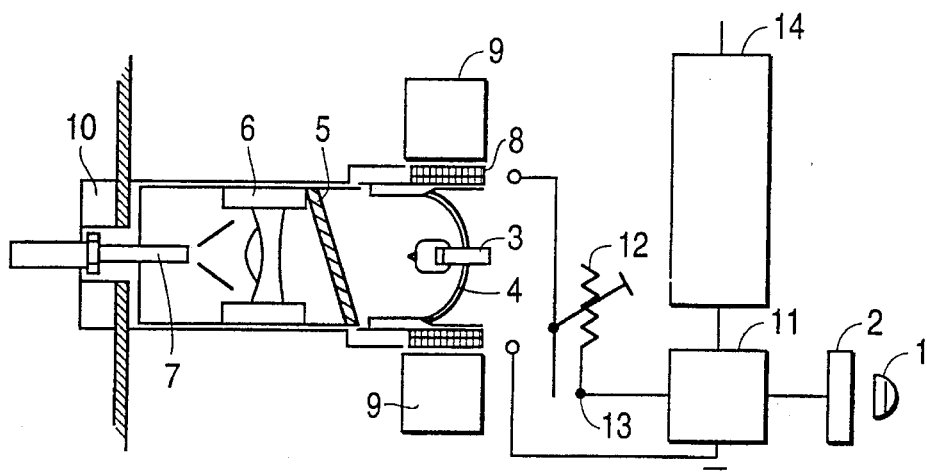
FIG. 1 relates to a first preferred embodiment of the present invention in which the lamp having a reflector is shifted, FIG. 2 relates to a second preferred embodiment of the present invention in which the condenser is shifted, FIG. 3 relates to a third preferred embodiment of the present invention in which the optical system arranged thereafter is shifted, FIG. 4 relates to a fourth preferred embodiment of the present invention with manual adjustment, FIG. 5 relates to a fifth preferred embodiment of the present invention with "shape memory shifting", FIG. 6 relates to a sixth preferred embodiment of the present invention in which the lamp having a reflector is pivoted, FIGS. 7 and 8 relates to preferred embodiments in which coupling-in the light into a fiberglass bundle occurs almost perpendicularly.

In the following, the present invention is described without the intention of limiting the scope or spirit of the overall inventive idea using an example of an illumination device for a video endoscope with reference to FIGS. 1 to 5. A video camera having a lens 1 and an image recorder 2 is provided at the proximal or distal end of a not depicted endoscope.

For illuminating the scene to be recorded by the video camera, an illumination device is provided which is made more apparent in the following:

A lamp 3 is arranged in a reflector 4, before which an IR blocking filter 5 is provided which is disposed diagonally to the optical axis of the reflector in the preferred embodiments depicted in FIGS. 1 to 5 so that the infrared radiation is reflected out of the beam path. The light passing the IR blocking filter 5 is focused by a condenser lens 6 onto a light guide 7 which guides the illumination light to the object (not shown) recorded by the video camera. The condenser lens 6 is provided with a convection cut in order to compensate for the dark spot of light in the beam paths of halogen lamps due to the using point.

In the illustrated first preferred embodiment, lamp 3 can be moved in conjunction with reflector 4 along the optical axis of the latter which corresponds with the optical axis of the condenser lens 6 and optical system 7 disposed thereafter by means of an electrodynamic system formed by a coil 8 and magnet 9. 10 stands for a housing part and the attachment thereto.

To coil 8 is applied a positioning signal which is generated by a light value-control unit, respectively regulation unit 11, which is disposed after the image recorder 2, or a manual regulator 12. A switch 13 is provided for switching between regulation and manual control. 14 stands for the camera electronics of a camera.

By moving lamp 3 in conjunction with reflector 4 surrounding the lamp in the direction of the optical axis of the condenser system 6, respectively the optical system 7 disposed thereafter, the position of the focus of the condenser system 6 in relation to the optical system 7 arranged thereafter and thus coupling-in light into the optical system varies, whereas a constant voltage, respectively constant power is preferably but not necessarily applied to the lamp so that its color temperature does not change.

Figure 2:
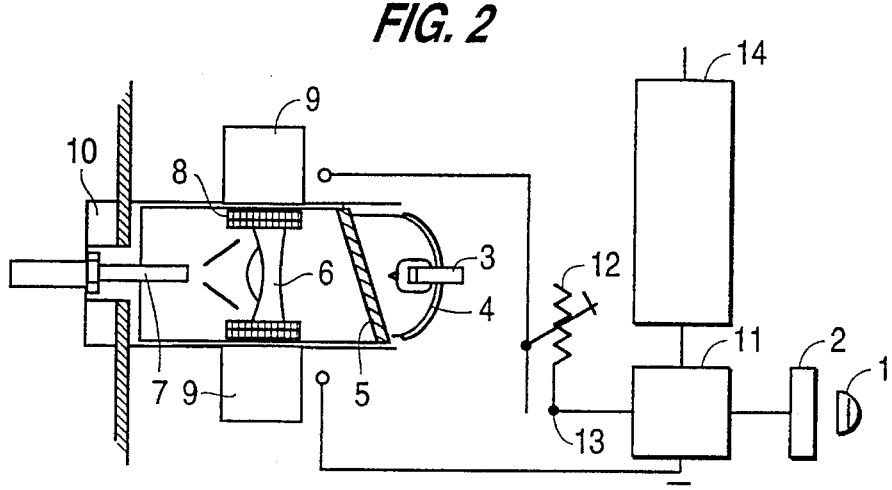

In the following figures the same reference numbers are used for the same or corresponding parts so that reintroduction is obviated and only the differences between the preferred embodiments depicted in these figures and the first preferred embodiment are explained:

FIG. 2 shows a second preferred embodiment of the present invention in which not lamp 3 but rather the condenser lens, respectively the condensor system 6 is moved by means of the electromagnetic system 8, 9 in direction of the optical axis of the optical systems. By this means the position of the focus of the condenser system 6 relative to the optical system 7 disposed thereafter is also varied and thus the coupling-in of the light into the optical system as well.

Figure 3:
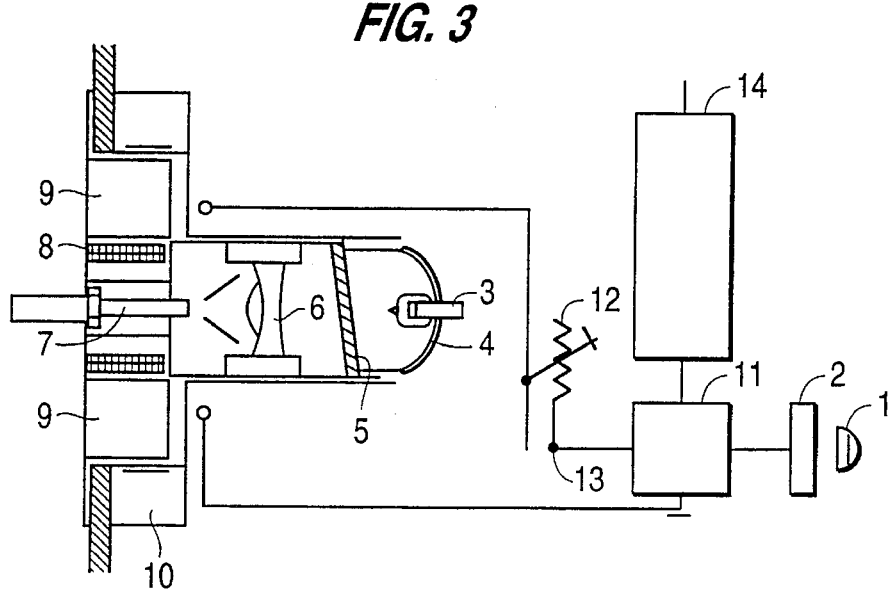

In the third preferred embodiment illustrated in FIG. 3, instead of condenser 6, the light guide 7 is moved in direction of the optical axis by the electromagnetic system 8, 9.

Figure 4:
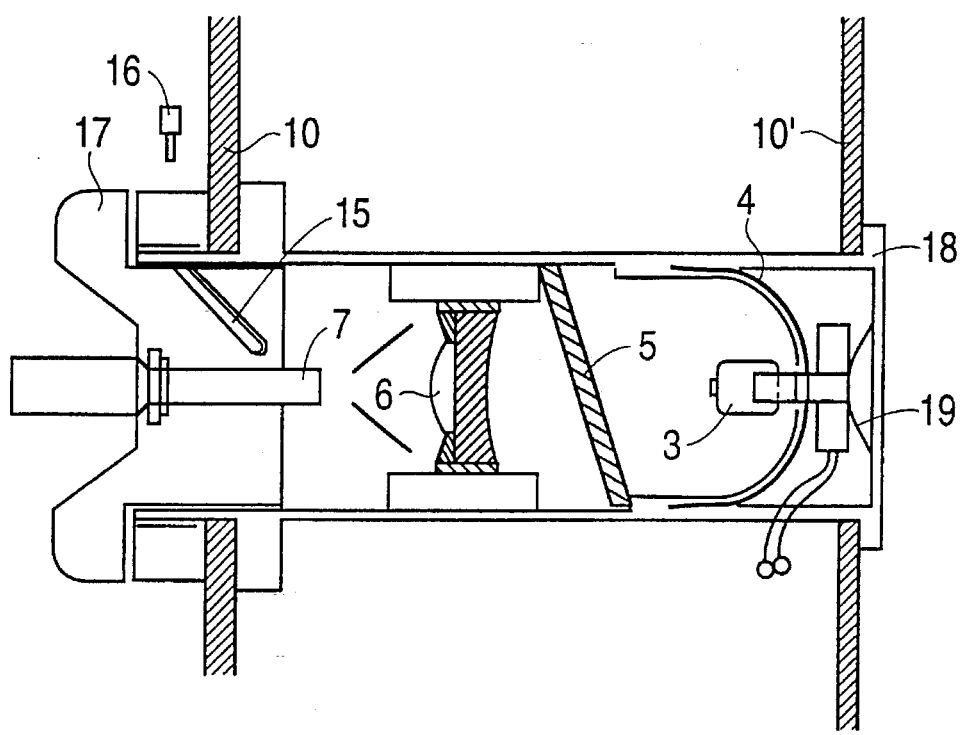

FIG. 4 shows a fourth preferred embodiment of the present invention in which the light guide 7 is manually moved in the direction of the optical axis. For this purpose an adjustment screw 15, a guide pin 16 and a turning knob are provided.

In the fourth preferred embodiment the lamp 3, furthermore, is held on a lamp adapter or changer 18 by a heat-expansion spring 19 by means of which contact problems due to varying expansion coefficients of the lamp 3 and the housing 10, respectively 10', are avoided.

Figure 5:
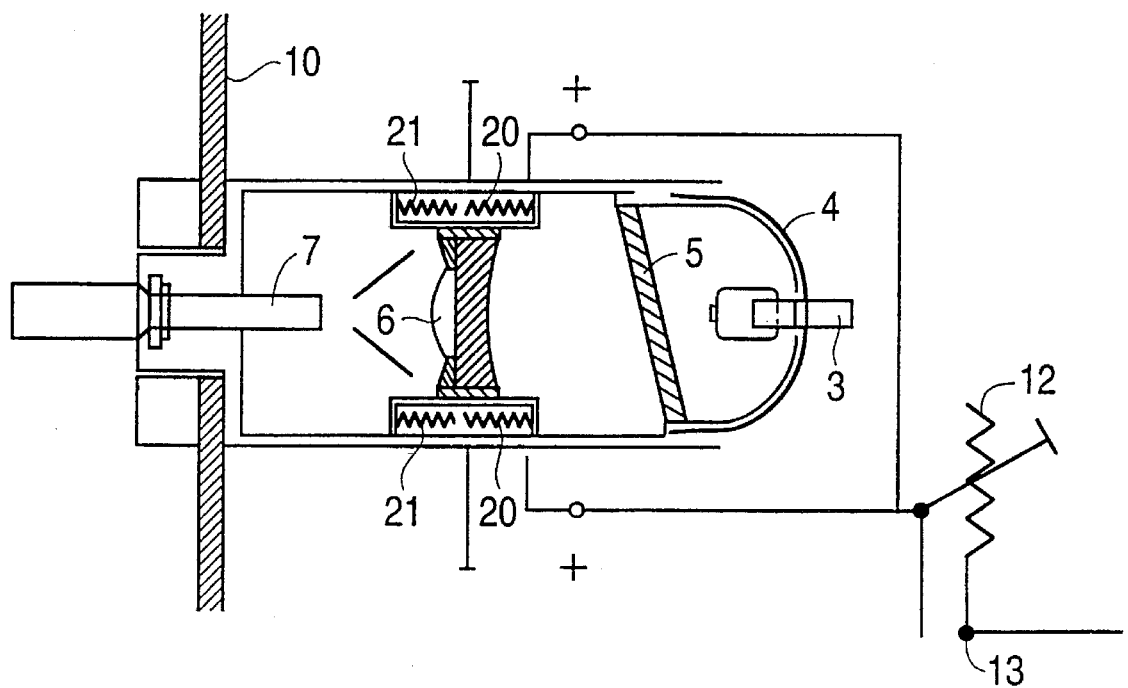

In the fifth preferred embodiment illustrated in FIG. 5, the condenser lenses 6 is moved by a shape-memory metal spring 20, which is heated by current flowing through it in such a manner that it expands. By reducing the current flowing through, a spring 21 presses the condenser lens 6 back again. By providing in the ilumination device a fan for cooling the lamp, additional rapid cooling of the spring 20 can be obtained so that short adjustment times are possible.

Figure 6:
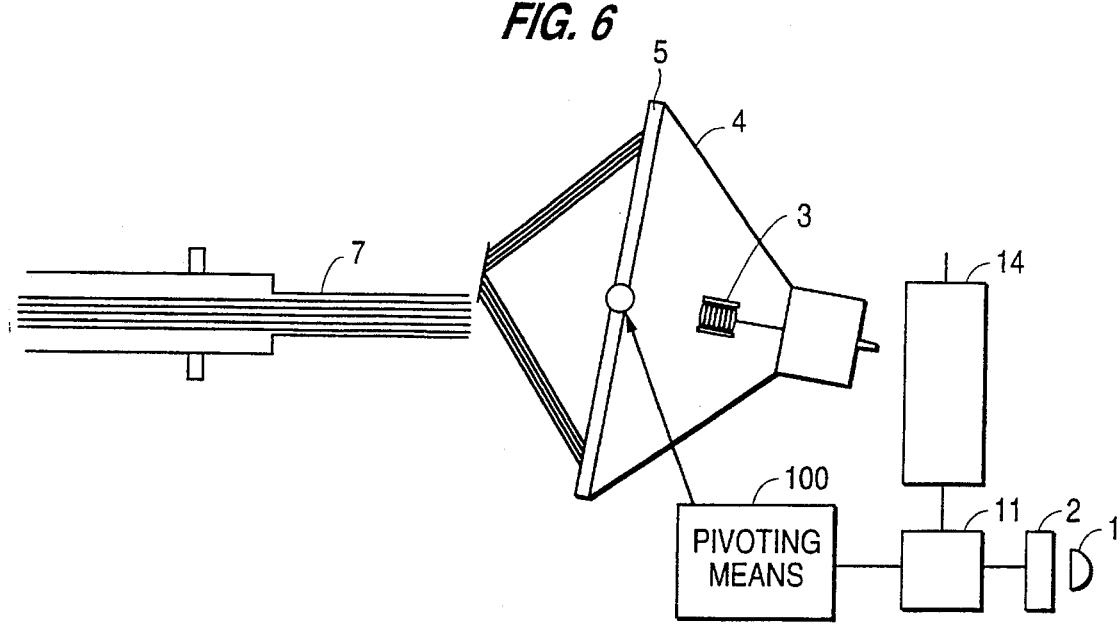

FIG. 6 shows a preferred embodiment of the present invention with no shifting but rather pivoting taking place via a pivoting means 100, in this event of lamp 3 including reflector the 4. By this means, too, a changing of the position of the lamp focus in relation to the fibreglass bundle 7 positioned thereafter occurs so that coupling-in the light into the fibreglass bundle again varies dependent on the pivoting angle. Naturally instead of pivoting, moving in the direction perpendicular to the optical axis may occur as well.

Figure 7:
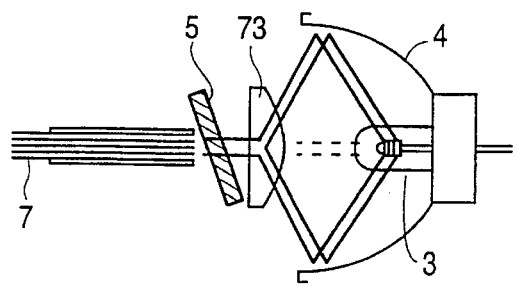

A solution to the problem arising in the condenser systems illustrated in FIGS. 1 to 6, which are provided with a reflector 4 for the light from lamp 3, is described in FIG. 7 and the following figures:

Due to the fusing point of lamp 3 which is usually centrally disposed, the light rays emerge from the reflector 4 at an angle to the optical axis and therefore also do not enter the light-entry surface(s) of the fiberglass bundles 7 perpendicularly so that there may be a considerable loss of light. In order to largely avoid this loss of light:

An inventive element is that means are provided which guide the light rays emerging from the reflector almost perpendicularly into the light-entry surface(s) of the fibreglass bundle.

In the preferred embodiment illustrated in FIG. 7, a lens 73 is provided which deflects the light from lamp 3 emerging from the reflector 4 on a surface of a cone in such a manner that it enters the fibreglass bundle 7 almost perpendicularly. This lens has preferably a surface which is not simply spherically curved but rather is provided with varyingly curved areas, thus several "calottes" which deflect the light on the surface of the cone into the optical axis of the system and, in particular of the fiberglass bundle.

Figure 8A:
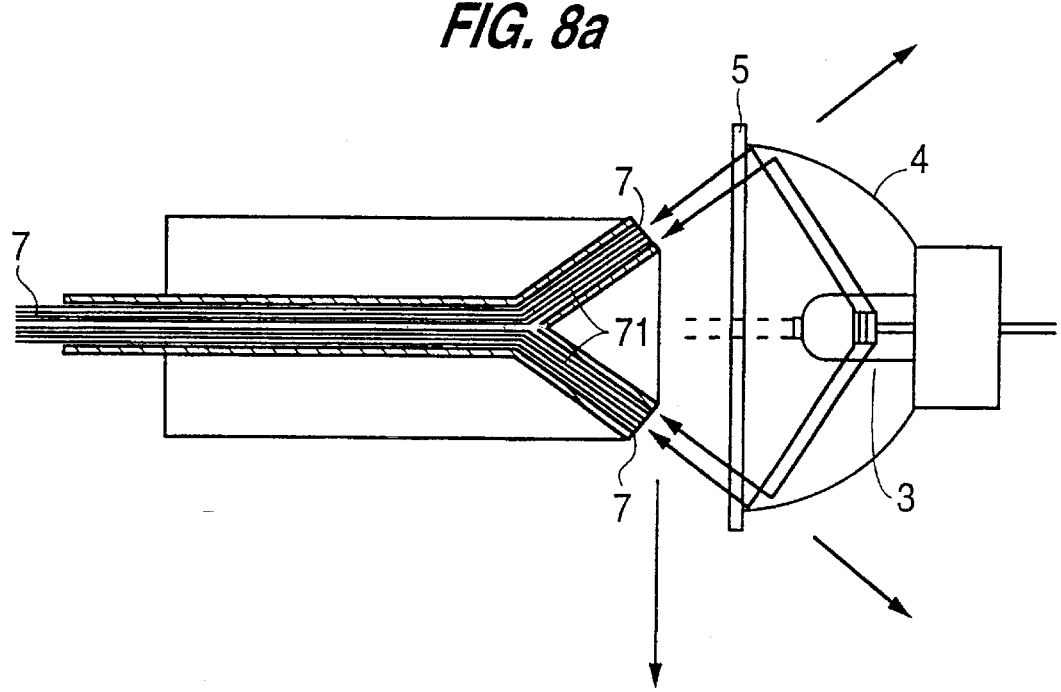
Figure 8B:
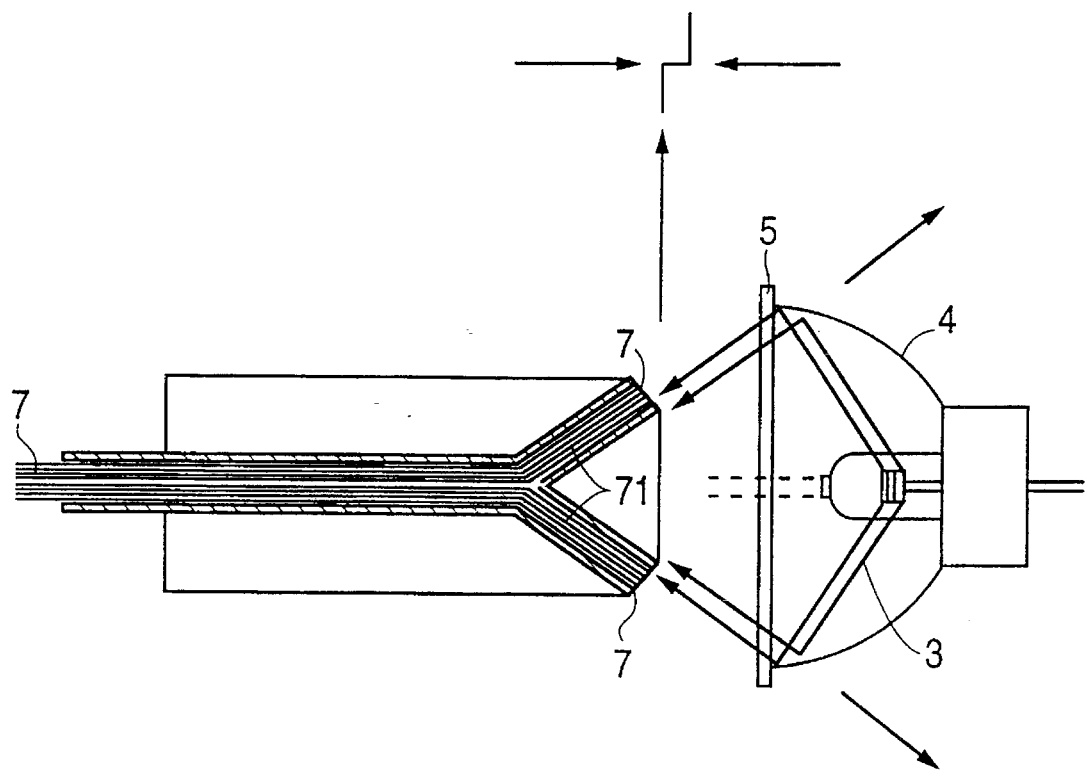

In the preferred embodiments illustrated in FIGS. 8a and 8b, the fiberglass bundle 7 is spread fan-like in such a manner that the single glass fibers 71 lie on the surface of a cone the opening angle of which is measured in such a manner that the light emerging from the reflector 4 enters the entry surfaces 72 of the glass fibers almost perpendicularly. By moving the fiberglass bundle 7 and/or the lamp 3 including the reflector 4, the coupling-in conditions can be finely adjusted with a short path so that a large regulating range is yielded with little mechanical effort.

What is claimed is:

1. A device using a fiber optic arrangement to transmit light for illuminating objects, in particular those objects to be recorded by a video camera, said device comprising:

at least one lamp;

a condenser system for condensing light from said at least one lamp;

an optical system including said fiber optic arrangement in a form of a fiberglass bundle which receives a condensed said light from said condenser system, and which directs said light onto an object or objects to be illuminated; and a control means for controlling the intensity of the illumination delivered to said fiberglass bundle and with which said object is illuminated while operating said at least one lamp at substantially a constant power, said control means controlling the intensity of illumination by selecting a focus of said condenser system relative to said optical system to multiple positions using automatic means for changing the focus of said condenser system.

2. A device as claimed in claim 1, further comprising a control unit activating said control means.

3. A device as claimed in claim 1, wherein said control means changes said position of focus by moving one of said at least one lamp, said condenser system and said optical system in a direction of an optical axis of said condenser system.

4. A device as claimed in claim 2, wherein said control means comprises an electrodynamic system for moving at least one of said at least one lamp, said condenser system and said optical system with respect to one another.

5. A device as claimed in claim 3, wherein said control means is a shape-memory element a temperature and shape of which can be adjusted by means of a heating element.

6. A device for illuminating objects, in particular those to be recorded by a video camera comprising:

at least one lamp;

a condenser system for condensing light from said at least one lamp;

an optical system which receives a condensed said light from said condenser system, and which directs said light onto an object or objects to be illuminated;

a control means for controlling the intensity of the illumination with which said object is illuminated while operating said at least one lamp at substantially a constant power, said control means controlling the intensity of illumination by changing a position of focus of said condenser system relative to said optical system; and characterized by a control signal which is derived from a video signal from a video camera being applied to said control means.

7. A device as claimed in claim 6, wherein said control signal is derived from an output signal of an image recorder before signal processing is performed by means of processing electronics of said video camera.

8. A device as claimed in any one of claims 1 to 6, wherein said control means further has constructions to permit manual movement of at least one of said at least one lamp, said condenser system and said optical system, for changing said position of focus.

9. A device as claimed in claim 7, wherein said constructions of said control means comprises a manual adjustment screw to permit manual movement of at least one of said at least one lamp, said condenser system and said optical system, for changing said position of focus.

10. A device as claimed in claim 4, wherein said control means comprises an adjustment device for adjusting a current flowing through said electrodynamic system.

11. A device as claimed in claim 1, further comprising an infrared-blocking filter interposed between said optical system and said at least one lamp to block infrared components from said at least one lamp from being delivered to said optical system.

12. A device as claimed in claim 11, characterized by said infrared-blocking filter being arranged at an angle unequal to 90° with respect to said optical axis of said condenser and said optical system.

13. A device as claimed in any one of claims 1 to 7, characterized by said at least one lamp being a halogen lamp.

14. A device as claimed in any one of claims 1 to 7, characterized by said at least one lamp being disposed in an adapter.

15. A device using a fiber optic arrangement to transmit light for illuminating objects, in particular those objects to be recorded by a video camera, said device comprising:

at least one lamp;

a condenser system for condensing light from said at least one lamp;

an optical system including said fiber optic arrangement in a form of a fiberglass bundle which receives a condensed said light from said condenser system, and which directs said light onto an object or objects to be illuminated; and a control means for controlling the intensity of the illumination fiberglass bundle and with which said object is illuminated while operating said at least one lamp at substantially a constant power, said control means controlling the intensity of illumination by changing a position of focus of said condenser system relative to said optical system;

wherein said condenser system is provided with a reflector from which rays of said light emerge at an angle to an optical axis of said condenser system, and said device further comprises guiding means which guide said rays of light emerging from said reflector to be incident almost perpendicularly into light-entry surfaces of said fiberglass bundle.

16. A device as claimed in claim 15, characterized by said guiding means being provided with a fan-like spreading of glass fibers in said fiberglass bundle in such a manner that said light emerging from said reflector enters into single glass fibers of the spread-out fiberglass bundle almost perpendicularly.

17. A device as claimed in claim 15, characterized by said guiding means being provided with at least one lens which deflects said light emerging from said reflector in such a manner that said light enters said fiberglass bundle almost perpendicularly.

18. A device as claimed in claim 17, characterized by said lens having a surface which is provided with varyingly curved areas.

19. A device as claimed in claim 15, characterized by said reflector being mirrored in an infrared-permeable manner.

20. A device using a fiber optic arrangement to transmit light for illuminating objects, in particular those objects to be recorded by a video camera, having at least one lamp, the light of which a condenser system projects onto an optical system which contains at least a glass fiber which transmits said light onto the object or objects to be illuminated, and a control means for adjusting the intensity level of the illumination with which said object is illuminated without changing the power with which the lamp is operated, by changing an arrangement of an illumination system to multiple positions using automatic means for changing the arrangement, said control means providing said controlling by performing one of: A.) moving one of said lamp, said condenser system and said optical system in one of the direction of and perpendicular to the optical axis of the condenser system, and B.) pivoting at least one of said lamp, said condenser system and said optical system relative to each other, such that the location of the focus of the condenser system is changed relatively to the optical system and thus, the intensity of light which is coupled into the optical system is varied.

21. A device as claimed in claim 1, wherein said control means changes said position of focus by pivoting one of said at least one lamp, said condenser system and said optical system with respect to one another.

22. A device as claimed in claim 1, wherein said control means changes said position of focus by moving one of said at least one lamp, said condenser system and said optical system in a direction perpendicular to an optical axis of said condenser system.

23. A device as claimed in claim 5, wherein said control means comprises an adjustment device for adjusting a current flowing through said heating element.

* * * * *